US011807722B2

(12) United States Patent
Tavernier et al.

(10) Patent No.: US 11,807,722 B2
(45) Date of Patent: Nov. 7, 2023

(54) PROCESS FOR MANUFACTURING A CROSS-LINKED PRODUCT

(71) Applicants: ARIANEGROUP SAS, Paris (FR); CENTRE NATIONAL DE LA RECHERCHE SCIENTIFIQUE, Paris (FR)

(72) Inventors: Romain Tavernier, Doullens (FR); Lérys Granado, Carcassonne (FR); Ghislain David, Montpellier (FR); Sylvain Caillol, Montpellier (FR); Gabriel Foyer, Le Haillan (FR)

(73) Assignees: ARIANEGROUP SAS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 462 days.

(21) Appl. No.: 17/036,603

(22) Filed: Sep. 29, 2020

(65) Prior Publication Data

US 2021/0095077 A1    Apr. 1, 2021

(30) Foreign Application Priority Data

Sep. 30, 2019   (FR) ..................... 1910775

(51) Int. Cl.
*C08G 73/22* (2006.01)
*B64G 1/14* (2006.01)
*B64G 1/40* (2006.01)

(52) U.S. Cl.
CPC .............. *C08G 73/22* (2013.01); *B64G 1/14* (2013.01); *B64G 1/40* (2013.01)

(58) Field of Classification Search
CPC ........ C08G 14/04; C08G 14/00; C08G 14/12; C08G 73/22; C08G 73/06; C08L 79/04; C08L 79/08; G03F 7/0387; G03F 7/0392; G03F 7/2004; G03F 7/322; G03F 7/40; B64G 1/14; B64G 1/40
See application file for complete search history.

(56) References Cited

U.S. PATENT DOCUMENTS

2010/0216900 A1 * 8/2010 Liu ..................... C08G 61/12
521/27

OTHER PUBLICATIONS

Search Report as issued in French Patent Application No. 1910775, dated Jun. 26, 2020.
Pereira, R. C. S., et al., "Influence of natural substituents in the polymerization of novel bio-based benzoxazines," Materials Today Communications, vol. 21, Sep. 2019, pp. 1-11, XP055707570.
Ohashi, S., et al., "Synthesis and ring-opening polymerization of 2-substituted 1,3-benzoxaine: the first observation of the polymerization of oxazine ring-substituted benzoxazines," Polymer Chemistry, vol. 7, No. 46, Jan. 2016, pp. 7177-7184, XP055626808.

(Continued)

*Primary Examiner* — Shane Fang
(74) *Attorney, Agent, or Firm* — Pillsbury Winthrop Shaw Pittman LLP

(57) ABSTRACT

A process for manufacturing a cross-linked product has improved charring and thermal stability properties in which there is cross-linking of a benzoxazine monomer.

9 Claims, 2 Drawing Sheets

(56) References Cited

OTHER PUBLICATIONS

Baqar, M., et al., "Methylol-Functional Benzoxazines as Precursors for High-Performance Thermoset Polymers: Unique Simultaneous Addition and Condensation Polymerization Behavior," Journal of Polymer Science Part A: Polymer Chemistry, vol. 50, No. 11, Jun. 2012, pp. 2275-2285, XP055174650.

Zhang, K., et al., "Polymerization of an AB-Type Benzoxazine Monomertoward Different Polybenzoxazine Networks: When Diels-Alder Reaction Meets Benzoxazine Chemistry in a Single-Component Resin," Macromolecules, vol. 52, No. 19, Sep. 2019, pp. 7386 7395, XP055707581.

Goto, M., et al., "Synthesis and Crosslinking Reaction of Polyacetylenes Substituted with Benzoxazine Rings: Thermally Highly Stable Benzoxazine Resins," Journal of Polymer Science Part A: Polymer Chemistry, vol. 56, No. 16, Aug. 2018, pp. 1884-1893, XP055707585.

Zhang, K., et al., "High performance crosslinked polyimide based on main-chain type polybenzoxazine," RSC Advances, vol. 4, No. 107, Jan. 2014, pp. 62550-62556, XP055707590.

Oie, H., et al., "Synthesis of Networked Polymers by Crosslinking Reactions of Polybenzoxazine Bearing Allyl Group in the Side Chain," Journal of Polymer Science Part A: Polymer Chemistry, vol. 51, No. 9, May 2013, pp. 2035-2039, XP055707593.

Agag, T., et al., "Crosslinked Polyamide Based on Main-Chain Type Polybenzoxazines Derived from a Primary Amine-Functionalized Benzoxazine Monomer," Journal of Polymer Science Part A: Polymer Chemistry, vol. 49, No. 20, Oct. 2011, pp. 4335-4342, XP055707599.

Chaisuwan, T., et al., "High-Performance Maleimide and Nitrile-Functionalized Benzoxazines with Good Processibility for Advanced Composites Applications," Journal of Applied Polymer Science, vol. 101, No. 1, Jan. 2006, pp. 548-558, XP055063540.

\* cited by examiner

[Fig. 1]
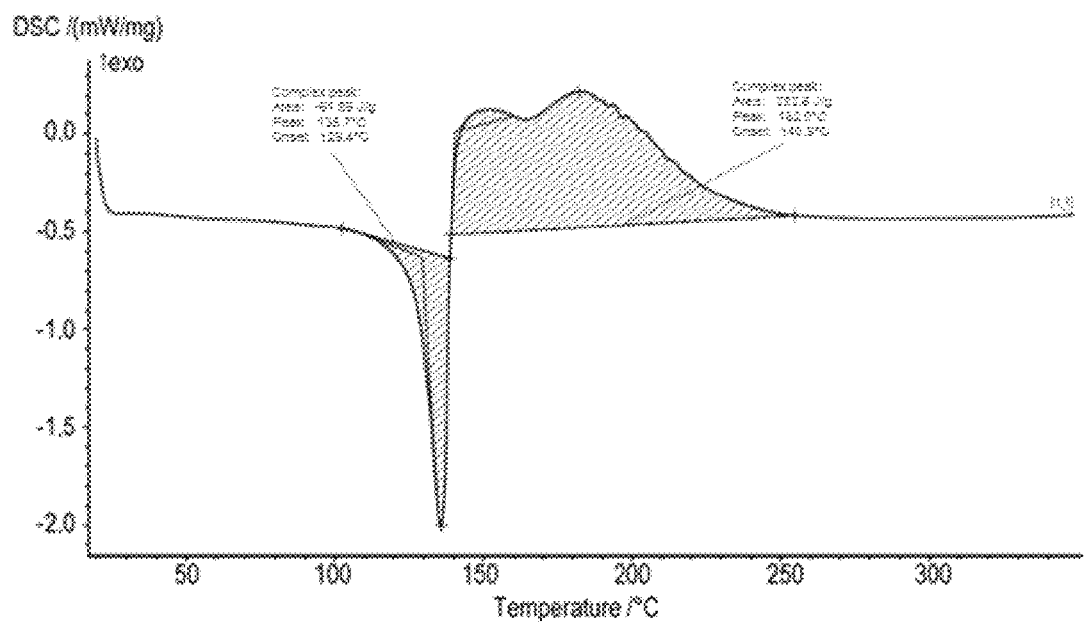
[Fig. 2]
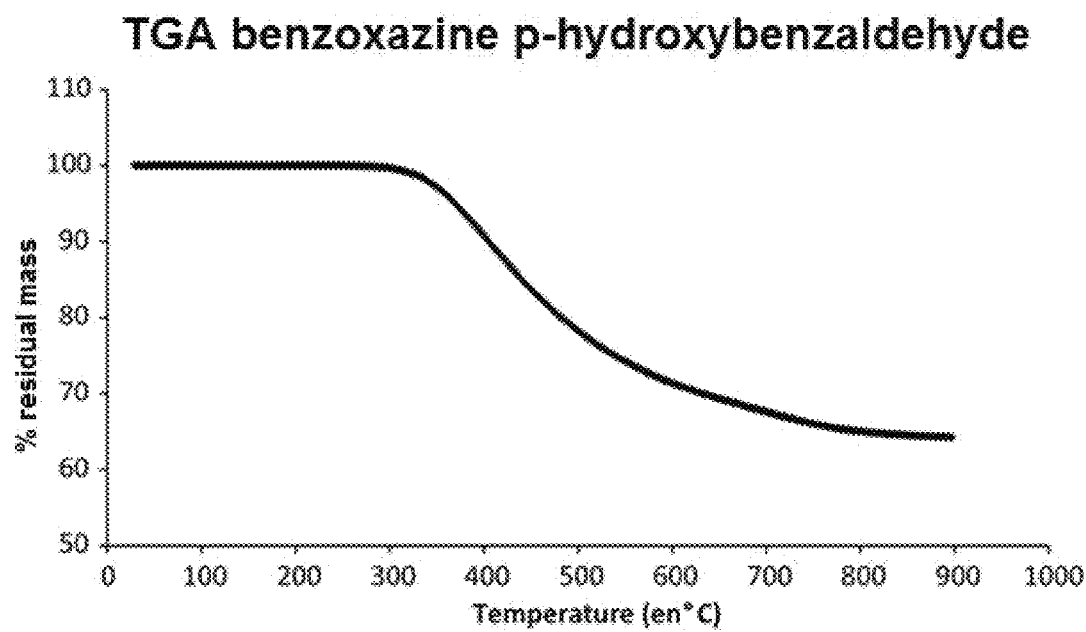

[Fig. 3]
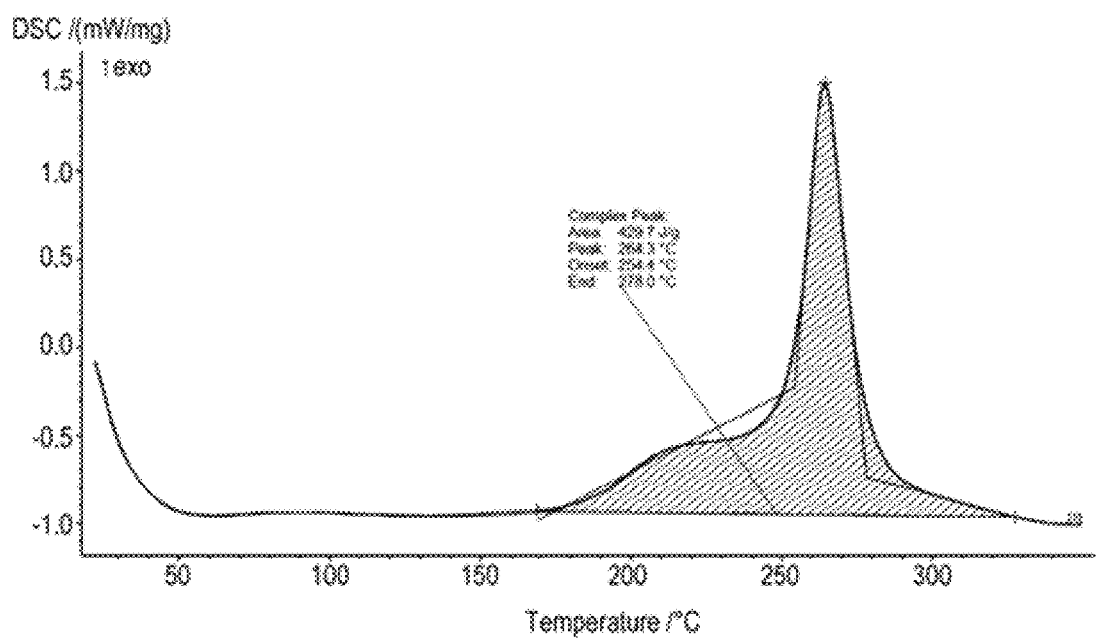
[Fig. 4]
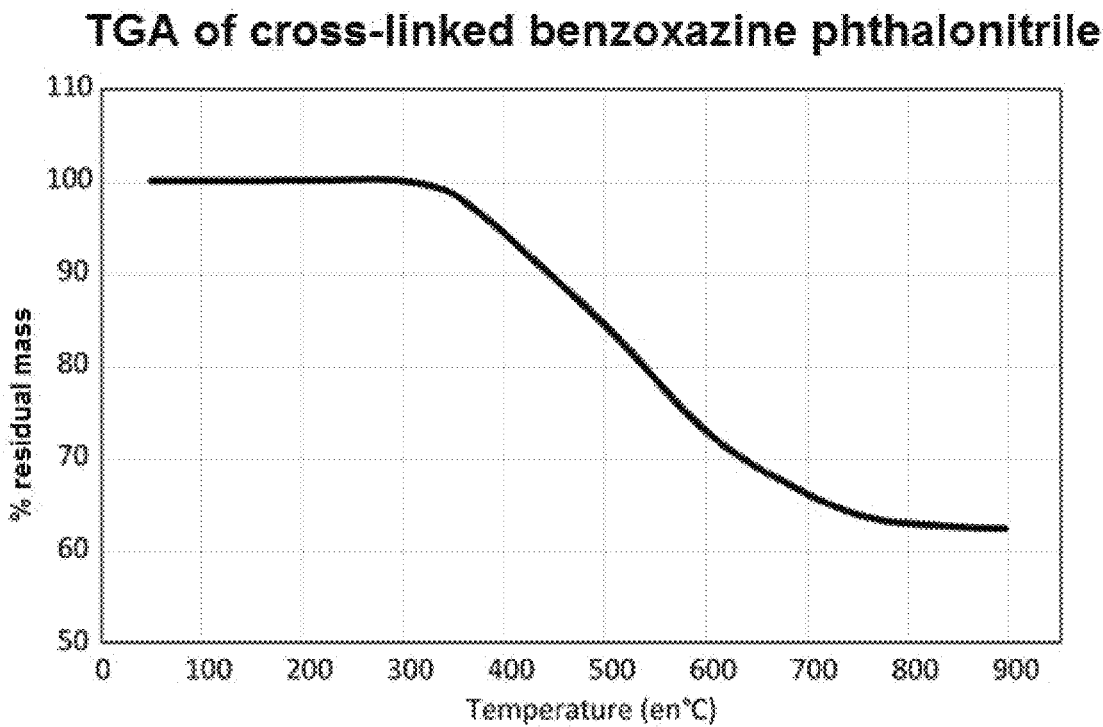

PROCESS FOR MANUFACTURING A CROSS-LINKED PRODUCT

CROSS REFERENCES TO RELATED APPLICATIONS

This application claims priority to French Patent Application No. 1910775, filed Sep. 30, 2019, the entire content of which is incorporated herein by reference in its entirety.

FIELD

The invention relates to a process for manufacturing a cross-linked product having improved charring and thermal stability properties. This cross-linked product can be used in particular as an ablative resin for the constitution of a rocket nozzle or a re-entry vehicle.

PRIOR ART

It is known to produce ablative thermal protections for rocket nozzles or re-entry vehicles from phenolic resins synthesized from formaldehyde and phenol, in order to obtain high aromatic and cross-linking densities and therefore a high coke rate. Formaldehyde and phenol are however classified as Carcinogenic Mutagenic Reprotoxic (CMR) Category 1B and 2 substances whose use should be limited, in particular in anticipation of possible prohibitions in the European Union.

Furthermore, the reaction of phenol and formaldehyde is a polycondensation which produces water. This water can become trapped within the finished product, leading to decreased performance. To resolve this problem, developments have been pursued to obtain ablative resins by cross-linking benzoxazines. These developments reduce water entrapment in the finished product, but solutions in the literature, providing a finished product with thermal stability and charring properties compatible with an application as an ablative resin, involve benzoxazines obtained by reacting phenol with formaldehyde and an amine, and are therefore based on the use of CMR-classified compounds. Moreover, when these benzoxazines are synthesized without phenol, they exhibit poor thermal stability and charring properties.

It would be desirable to have a new way of synthesizing materials with thermal stability and charring properties adapted to the production of ablative thermal protections for rocket nozzles or re-entry vehicles.

SUMMARY

An aspect of the invention provides, according to a first embodiment, a process for manufacturing a cross-linked product comprising the cross-linking of a benzoxazine monomer of formula A provided below:

[Chem. 1]

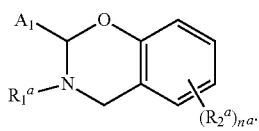

in this formula:

$A_1$ is selected from: (i) saturated, unsaturated or aromatic, monocyclic or polycyclic carbocyclic or heterocyclic groups, substituted by a cross-linkable group, (ii) saturated or unsaturated, linear or branched hydrocarbon chains, optionally interrupted by one or more heteroatoms, substituted by a cross-linkable group, in the alternative (i) or (ii) said cross-linkable group is selected from: a hydroxyl group, an amine group, a maleimide group, an acetylene group, an allyl group, a carbonitrile group, a phthalimide group, a phthalonitrile group, an epoxide group, for example an oxirane group, $R_1^a$ is selected from: substituted or unsubstituted furfuryl groups, saturated, unsaturated or aromatic, monocyclic or polycyclic, substituted or unsubstituted carbocyclic or heterocyclic groups, substituted or unsubstituted aralkyl groups, linear or branched, saturated or unsaturated, substituted or unsubstituted hydrocarbon chains, optionally interrupted by one or more heteroatoms, $n^a$ is an integer comprised between 0 and 2, $R_2^a$ is selected from: electron-withdrawing groups, saturated or unsaturated, substituted or unsubstituted, linear or branched hydrocarbon chains comprising between 1 and 6 carbon atoms, optionally interrupted by one or more heteroatoms, saturated, unsaturated or aromatic, substituted or unsubstituted carbocyclic or heterocyclic groups.

The invention provides, according to a second embodiment, a process for manufacturing a cross-linked product comprising the cross-linking of a benzoxazine monomer of formula B provided below:

[Chem. 2]

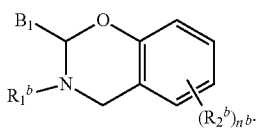

in this formula:

$B_1$ is selected from: substituted or unsubstituted furfuryl groups, saturated, unsaturated or aromatic, monocyclic or polycyclic, substituted or unsubstituted carbocyclic or heterocyclic groups, substituted or unsubstituted aralkyl groups, linear or branched, saturated or unsaturated, substituted or unsubstituted hydrocarbon chains, optionally interrupted by one or more heteroatoms, $R_1^b$ is selected from: (i) saturated, unsaturated or aromatic, monocyclic or polycyclic carbocyclic or heterocyclic groups, substituted by a cross-linkable group, (ii) saturated or unsaturated, linear or branched hydrocarbon chains, interrupted by one or more heteroatoms or by one or more saturated, unsaturated or aromatic, monocyclic or polycyclic carbocyclic or heterocyclic groups, substituted or unsubstituted, or uninterrupted, and substituted by a cross-linkable group, (iii) a cross-linkable group, in the alternative (i), (ii) or (iii) said cross-linkable group is selected from: a hydroxyl group, an amine group, an acetylene group, an allyl group, a maleimide group, a carbonitrile group, a phthalimide group, a phthalonitrile group, an epoxy group, for example an oxirane group, $n^b$ is an integer comprised between 0 and 2, $R_2^b$ is selected from: electron-withdrawing groups, saturated or unsaturated, substituted or unsubstituted, linear or branched hydrocarbon chains comprising between 1 and 6 carbon atoms, optionally interrupted by one or more heteroatoms, saturated, unsaturated or aromatic, substituted or unsubstituted carbocyclic or heterocyclic groups.

In its two embodiments described above, the invention proposes the use of benzoxazine monomers having a cross-linkable group making it possible to obtain, after cross-linking, a product having high thermal stability and charring properties, compatible with application as an ablative resin for the manufacture of a rocket nozzle or a re-entry vehicle. The invention provides a new way of synthesizing ablative resins which limits the use of CMR compounds, and in particular avoiding the use of formaldehyde.

In an exemplary embodiment, $A_1$ or $R_1^b$ is a monocyclic or polycyclic aromatic carbocyclic or aromatic heterocyclic group substituted by the cross-linkable group. The choice of such groups beneficially makes it possible to obtain, after cross-linking of the benzoxazine monomer, a product with improved thermal stability and charring properties.

In particular, $A_1$ or $R_1^b$ may be a benzene ring substituted by the cross-linkable group.

Alternatively, $A_1$ or $R_1^b$ can be a linear or branched hydrocarbon chain. The number of carbon atoms of this hydrocarbon chain can vary widely, $A_1$ or $R_1^b$ can comprise between 1 and 20 carbon atoms or be a polymer.

According to an example and whatever the embodiment considered, the cross-linkable group is a hydroxyl group.

In an exemplary embodiment, $R_1^a$ or $B_1$ is selected from: substituted or unsubstituted furfuryl groups, monocyclic or polycyclic, substituted or unsubstituted carbocyclic aromatic or heterocyclic aromatic groups, substituted or unsubstituted aralkyl groups.

The choice of such groups beneficially makes it possible to obtain, after cross-linking of the benzoxazine monomer, a product with improved thermal stability and charring properties.

In particular, $R_1^a$ or $B_1$ may be a substituted or unsubstituted furfuryl group.

The presence of oxygen from the furfuryl ring, by accepting hydrogen bonds, provides increased stabilization of the cross-linked network, thus further increasing the charring rate.

Alternatively, $R_1^a$ or $B_1$ can be a linear or branched hydrocarbon chain. The number of carbon atoms in this hydrocarbon chain can vary widely. For example, $R_1^a$ or $B_1$ can be a linear or branched hydrocarbon chain with 1 to 20 carbon atoms or be a polymer.

In an exemplary embodiment, $n^a$ or $n^b$ is equal to 0.

In the variant where $n^a$ is non-zero, $R_2^a$ may in particular be selected from: alkoxy groups, carboxyl groups, halogen atoms, saturated or unsaturated, substituted or unsubstituted, linear or branched hydrocarbon chains comprising between 1 and 6 carbon atoms, optionally interrupted by one or more heteroatoms, saturated or unsaturated or aromatic, substituted or unsubstituted carbocyclic or heterocyclic groups.

In the variant where $n^b$ is non-zero, $R_2^b$ may in particular be selected from: alkoxy groups, carboxyl groups, halogen atoms, saturated or unsaturated, substituted or unsubstituted, linear or branched hydrocarbon chains comprising between 1 and 6 carbon atoms, optionally interrupted by one or more heteroatoms, saturated or unsaturated or aromatic, substituted or unsubstituted carbocyclic or heterocyclic groups.

According to an example of the first embodiment, the process comprises, prior to the cross-linking of the benzoxazine monomer of formula A, the condensation of an amine of formula A11 with an aldehyde of formula A12 to obtain the benzoxazine monomer of formula A, formulas A11 and A12 being provided below:

[Chem. 3]

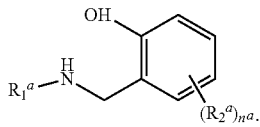

A11

[Chem. 4]

A12

In particular, the process may comprise, prior to the condensation, obtaining the amine of formula A11, this obtaining comprising:

an addition reaction of an amine of formula A21 with an aldehyde of formula A22 to form an imine of formula A23, and a reduction reaction of the imine of formula A23 to the amine of formula A11, formulas A21, A22 and A23 being provided below:

[Chem. 5]

A21

[Chem. 6]

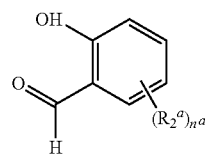

A22

[Chem. 7]

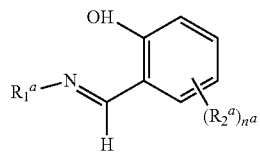

A23

The amine of formula A21 is for example selected from the following compounds: furfurylamine, benzylamine or 1-aminobutan-2ol.

The aldehyde of formula A22 can for example be salicylaldehyde. The aldehyde of formula A22 can be a monoaldehyde, i.e. comprising only one aldehyde function.

The aldehyde of formula A12 is for example selected from the following compounds: hydroxybenzaldehyde, for example para-hydroxybenzaldehyde, vanillin, syringaldehyde, aminobenzaldehyde, for example para-aminobenzaldehyde, maleimide-benzaldehyde, for example N-(4-formylphenyl)maleimide, phthalimide-benzaldehyde, for example para-phthalimidebenzaldehyde or phthalonitrile-benzaldehyde, for example para-phthalonitrile-benzaldehyde.

In another example of the first embodiment, the process comprises, prior to the cross-linking of the benzoxazine monomer of formula A:

the condensation of the amine of formula A11 with an aldehyde of formula A13 to obtain a benzoxazine precursor of formula A14, formula A11 being defined above and formulas A13 and A14 being provided below:

[Chem. 8]

A13

[Chem. 9]

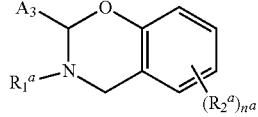

A14 where $A_3$ denotes a precursor group making it possible to obtain the function $A_1$ carrying the cross-linkable group after a functionalization reaction, and carrying out the functionalization reaction of the benzoxazine precursor of formula A14 in order to obtain the benzoxazine monomer of formula A.

The aldehyde of formula A13 is for example selected from the following compounds: hydroxybenzaldehyde, for example para-hydroxybenzaldehyde, vanillin, syringaldehyde, aminobenzaldehyde, for example para-aminobenzaldehyde.

The hydroxyl and amine groups may be cross-linkable groups as described above or may be precursor groups to other cross-linkable groups.

According to an example of the second embodiment, the process comprises, prior to the cross-linking of the benzoxazine monomer of formula B, the condensation of an amine of formula B11 with an aldehyde of formula B12 to obtain the benzoxazine monomer of formula B, formulas B11 and B12 being provided below:

[Chem. 10]

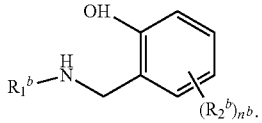

B11

[Chem. 11]

B12

In particular, the process may comprise, prior to the condensation, obtaining the amine of formula B11, this obtaining comprising:

an addition reaction of an amine of formula B21 on an aldehyde of formula B22 in order to form an imine of formula B23, and a reduction reaction of the imine of formula B23 to the amine of formula B11, formulas B21, B22 and B23 being provided below:

[Chem. 12]

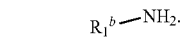

B21

[Chem. 13]

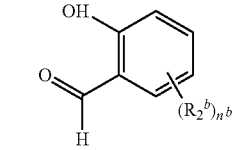

B22

[Chem. 14]

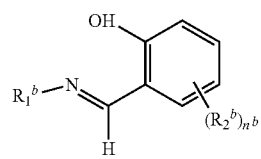

B23

The amine of formula B21 is for example selected from the following compounds: allylamine, aminophthalonitrile, for example 4-aminophthalonitrile, aminoacetylene, aminobenzonitirile, for example 4-aminobenzonitirile.

The aldehyde of formula B22 can for example be salicylaldehyde. The aldehyde of formula B22 can be a monoaldehyde, i.e. comprising only one aldehyde function. The aldehyde of formula B12 is for example selected from the following compounds: benzaldehyde, phenylacetaldehyde.

In another example of the second embodiment, the process comprises, prior to the cross-linking of the benzoxazine monomer of formula B:

the condensation of an amine of formula B13 with the aldehyde of formula B12 in order to obtain a benzoxazine precursor of formula B14, formula B12 being defined above and formulas B13 and B14 being provided below:

[Chem. 15]

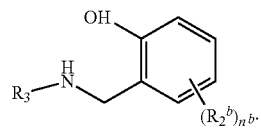

B13

[Chem. 16]

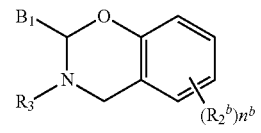

B14 where $R_3$ denotes a precursor group making it possible to obtain the function $R_1^b$ carrying the cross-linkable group after a functionalization reaction, and carrying out the functionalization reaction of the benzoxazine precursor of formula B14 in order to obtain the benzoxazine monomer of formula B.

The amine of formula B13 is for example obtained by addition of an amine $R_3$—$NH_2$ to an aldehyde of formula B22 described above to obtain the corresponding imine which is then reduced to obtain the amine of formula B13. The amine of formula $R_3$—$NH_2$ can for example be selected from the following compounds: xylyldiamine for example metaxylylenediamine, a phenylenediamine for example paraphenylenediamine, an aminophenol for example para-aminophenol.

Whatever the example considered, the condensation can be carried out by bringing the mixture of amine and aldehyde to reflux. The condensation can be carried out in toluene, methanol, ethanol or without solvent.

An aspect of the invention also relates to a rocket nozzle obtained by using a cross-linked product obtained by the process described above. Another aspect of the invention also relates to a process for manufacturing a rocket nozzle in which the nozzle is manufactured using a cross-linked product obtained by the process described above.

The rocket nozzle can be made of composite material. In this case, the manufacture of the nozzle may include a first step of forming a fibrous preform of the nozzle to be obtained impregnated with the benzoxazine monomer of formula A or B described above. This manufacture may also include a second step of heat treatment of the impregnated fibrous preform so as to cross-link the benzoxazine monomer of formula A or B and obtain the rocket nozzle.

The fibrous preform can for example be composed of carbon, silica, glass or ceramic material, for example silicon carbide. The fibrous preform intended to form the fibrous reinforcement of the nozzle can be formed in various ways (draping of pre-impregnated fabric layers, for example). In particular, two-dimensional or three-dimensional layers of impregnated fabric can be draped or wound onto a shape having a surface reproducing the desired geometry of an inner or outer surface of the nozzle to be made in order to obtain the impregnated preform.

Alternatively, it is possible to first obtain the fibrous preform of the nozzle to be obtained, then place this preform in an injection cavity and then inject the benzoxazine monomer of formula A or B into the cavity so as to impregnate the preform. In this case, a resin transfer molding technique can be used to impregnate the fibrous preform.

Cross-linking can be carried out by imposing a temperature greater than or equal to 130° C., for example comprised between 180° C. and 250° C.

Alternatively, an aspect of the invention also relates to a re-entry vehicle obtained by using a cross-linked product obtained by the process described above. Another aspect of the invention also relates to a process for manufacturing a re-entry vehicle in which the re-entry vehicle is manufactured using a cross-linked product obtained by the process described above.

Whatever the embodiment considered, the cross-linking used to obtain the cross-linked product may be a homo-cross-linking of the benzoxazine monomer of formula A or B on itself.

BRIEF DESCRIPTION OF THE DRAWINGS

FIG. 1 is a thermogram obtained by differential scanning calorimetry (DSC) of a first example of benzoxazine monomer according to the invention.

FIG. 2 is a result of thermogravimetric analysis (TGA) of a cross-linked product obtained by cross-linking this first example of benzoxazine monomer.

FIG. 3 is a DSC thermogram of a second example of benzoxazine monomer according to the invention.

FIG. 4 is a thermogravimetric analysis result of a cross-linked product obtained by cross-linking this second example of benzoxazine monomer.

DETAILED DESCRIPTION

EXAMPLES

Example 1: Synthesis of a Benzoxazine Monomer from Furfurylaminomethylphenol and Para-Hydroxybenzaldehyde and Subsequent Cross-Linking Furfurylamine is reacted with salicylaldehyde in stoichiometric proportions in methanol at reflux for 2 in order to form the corresponding imine. The imine is reduced to an amine with 1 equivalent of $NaBH_4$ added at 0° C. in a solution of the imine in MeOH, followed by heating at reflux for 2 hours. The furfurylaminomethylphenol thus synthesized is dissolved in toluene with 1 equivalent of para-hydroxybenzaldehyde, then refluxed in a Dean Stark apparatus to remove the water generated during the condensation reaction. The reaction is stopped when the conversion of aldehydes has reached its maximum, followed by proton NMR.

After evaporation of the solvent under reduced pressure, the isolated benzoxazine is a pale yellow solid. The product was characterized by NMR and infrared spectroscopy and the structure was confirmed.

Thermal characterization by DSC revealed a melting temperature of 130° C. as well as an exothermic reaction between 140° C. and 250° C. corresponding to cross-linking, representing 2833 J/g enthalpy with respect to the reference, with a ramp rate of 10° C./min in high-pressure sealed steel crucibles. The resulting DSC thermogram is shown in FIG. 1.

Thermogravimetric analysis showed a coke rate after in situ polymerization of 64% under nitrogen atmosphere, as well as a degradation temperature of 10% of the total mass of 402° C. (heating ramp rate: 10° C./min). This shows excellent thermal stability for this resin. The thermogravimetric analysis graph obtained is provided in FIG. 2.

Example 2: Synthesis of a Benzoxazine Monomer from Furfurylaminomethylphenol and Para-Phthalonitrile-Benzaldehyde and Subsequent Cross-Linking Para-hydroxybenzaldehyde is reacted with 1 equivalent of $K_2CO_3$ in dimethylformamide at 0° C. 1.1 equivalent of 4-nitrophthalonitrile is added gradually at 0° C. It is left stirring at room temperature overnight. The reaction medium is then precipitated in 50 times the volume of ice water. The heterogeneous yellow-colored medium is then filtered under vacuum, and an off-white viscous solid is obtained. This solid is dissolved in dichloromethane and washed 3 times with a saturated sodium chloride solution. The organic phase is isolated, dried over magnesium sulfate and the product recovered by evaporation of the solvent under reduced pressure. The product is an off-white powder.

The furfurylamine is reacted with salicylaldehyde in stoichiometric proportions in methanol at reflux for 2 h, in order to form the corresponding imine. The imine is reduced to an amine with 1 equivalent of $NaBH_4$ added at 0° C. in a solution of the imine in MeOH, followed by heating at reflux for 2 hours. The furfurylaminomethylphenol thus synthesized is dissolved in toluene with 1 equivalent of para-phthalonitrile-benzaldehyde, then refluxed in a Dean Stark apparatus to remove the water generated during the condensation reaction. The reaction is stopped when the aldehyde conversion has reached its maximum, followed by proton NMR. After evaporation of the solvent under reduced pressure, the isolated benzoxazine is an off-white viscous solid. The product was characterized by NMR and the structure was confirmed.

Thermal characterization by DSC revealed an exothermic reaction between 170° C. and 278° C., representing 4303 J/g of enthalpy relative to the reference, with a ramp rate of 10° C./min in high-pressure sealed steel crucibles. The resulting DSC thermogram is shown in FIG. 3.

The thermogravimetric analysis showed a coke rate after in situ polymerization of 62% under nitrogen atmosphere, as well as a degradation temperature of 10% of the total mass of 444° C. (heating ramp rate: 10° C./min). The thermogravimetric analysis graph obtained is provided in FIG. 4.

The invention claimed is:

1. A process for manufacturing a cross-linked product comprising the cross-linking of a benzoxazine monomer of formula A provided below:

[Chem. 17]

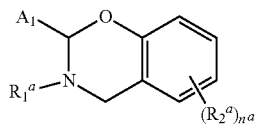

in this formula:
A$_1$ is selected from: (i) saturated, unsaturated or aromatic, monocyclic or polycyclic carbocyclic or heterocyclic groups, substituted by a cross-linkable group, (ii) saturated or unsaturated, linear or branched hydrocarbon chains, optionally interrupted by one or more heteroatoms, substituted by a cross-linkable group, in the alternative (i) or (ii), said cross-linkable group is selected from: a hydroxyl group, an amine group, a maleimide group, an acetylene group, an allyl group, a carbonitrile group, a phthalimide group, a phthalonitrile group, an epoxy group, R$_1^a$ is selected from: substituted or unsubstituted furfuryl groups, saturated, unsaturated or aromatic, monocyclic or polycyclic, substituted or unsubstituted carbocyclic or heterocyclic groups, substituted or unsubstituted aralkyl groups, linear or branched, saturated or unsaturated, substituted or unsubstituted hydrocarbon chains, optionally interrupted by one or more heteroatoms, n$^a$ is an integer comprised between 0 and 2, R$_2^a$ is selected from: electron-withdrawing groups, saturated or unsaturated, substituted or unsubstituted, linear or branched hydrocarbon chains comprising between 1 and 6 carbon atoms, optionally interrupted by one or more heteroatoms, saturated, unsaturated or aromatic, substituted or unsubstituted carbocyclic or heterocyclic groups.

2. The process as claimed in claim 1, wherein A$_1$ is a monocyclic or polycyclic aromatic carbocyclic or aromatic heterocyclic group substituted by the cross-linkable group.

3. The process as claimed in claim 2, wherein A$_1$ is a benzene ring substituted by the cross-linkable group.

4. The process as claimed in claim 1, wherein the cross-linkable group is a hydroxyl group.

5. The process as claimed in claim 1, wherein R$_1^a$ is selected from: substituted or unsubstituted furfuryl groups, monocyclic or polycyclic, substituted or unsubstituted carbocyclic aromatic or heterocyclic aromatic groups, substituted or unsubstituted aralkyl groups.

6. The process as claimed in claim 5, wherein R$_1^a$ is a substituted or unsubstituted furfuryl group.

7. The process as claimed in claim 1, wherein n$^a$ is equal to 0.

8. A rocket nozzle obtained by using a cross-linked product obtained by the process as claimed in claim 1.

9. A re-entry vehicle obtained by using a cross-linked product obtained by the process as claimed in claim 1.

* * * * *